(12) United States Patent
Lee

(10) Patent No.: US 10,603,495 B2
(45) Date of Patent: Mar. 31, 2020

(54) CURRENT SENSING MULTIPLE OUTPUT CURRENT STIMULATORS

(71) Applicant: ALFRED E. MANN FOUNDATION FOR SCIENTIFIC RESEARCH, Santa Clarita, CA (US)

(72) Inventor: Edward K.F. Lee, Fullerton, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 0 days.

(21) Appl. No.: 15/980,642

(22) Filed: May 15, 2018

(65) Prior Publication Data
US 2019/0015664 A1    Jan. 17, 2019

Related U.S. Application Data

(60) Continuation of application No. 15/263,046, filed on Sep. 12, 2016, now Pat. No. 9,981,130, which is a
(Continued)

(51) Int. Cl.
  *A61N 1/36* (2006.01)
  *H03K 3/012* (2006.01)
  *H03K 3/023* (2006.01)

(52) U.S. Cl.
  CPC ..... *A61N 1/36125* (2013.01); *A61N 1/36071* (2013.01); *A61N 1/36146* (2013.01);
  (Continued)

(58) Field of Classification Search
  CPC ... A61N 1/08; A61N 1/36125; A61N 1/36071
  (Continued)

(56) References Cited

U.S. PATENT DOCUMENTS

| 3,646,940 A | 3/1972 | Timm et al. |
| 3,942,535 A | 3/1976 | Schulman et al. |
| (Continued) | | |

FOREIGN PATENT DOCUMENTS

| CN | 1956750 | 5/2007 |
| CN | 105164920 | 12/2015 |
| (Continued) | | |

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.
(Continued)

*Primary Examiner* — Brian T Gedeon
*Assistant Examiner* — Philip C Edwards
(74) *Attorney, Agent, or Firm* — Kilpatrick Townsend & Stockton LLP

(57) ABSTRACT

A multiple output current stimulator circuit with fast turn on time is described. At least one pair of input side and output side transistors is arranged in a current mirror connected to a supply transistor by cascode coupling. The output side transistor supplies stimulation current to an electrode in contact with tissue. An operational amplifier connected to a reference voltage and to the output side transistor drives the supply transistor to maintain the voltage at the output side transistor equal to the reference voltage. The at least one pair of transistors includes multiple pairs of transistors whose output side transistors drive respective electrodes with stimulation currents. The stimulator determines the initiation and duration of stimulation current pulses supplied to each electrode. At circuit activation, large currents are generated
(Continued)

which discharge capacitances in the output side transistors causing rapid output side transistor turn on.

17 Claims, 8 Drawing Sheets

Related U.S. Application Data division of application No. 14/217,321, filed on Mar. 17, 2014, now Pat. No. 9,446,241.

(60) Provisional application No. 61/788,871, filed on Mar. 15, 2013.

(52) U.S. Cl.
CPC ............ *H03K 3/012* (2013.01); *H03K 3/023* (2013.01); *A61N 1/36003* (2013.01); *A61N 1/3605* (2013.01); *Y10T 307/406* (2015.04)

(58) Field of Classification Search
USPC .................................................. 607/34, 46
See application file for complete search history.

(56) References Cited

U.S. PATENT DOCUMENTS

| | | |
|---|---|---|
| 4,019,518 A | 4/1977 | Maurer et al. |
| 4,044,774 A | 8/1977 | Corbin et al. |
| 4,082,097 A | 4/1978 | Mann et al. |
| 4,340,062 A | 7/1982 | Thompson et al. |
| 4,468,723 A | 8/1984 | Hughes |
| 4,558,702 A | 12/1985 | Barreras et al. |
| 4,673,867 A | 6/1987 | Davis |
| 4,744,371 A | 5/1988 | Harris |
| 5,143,089 A | 9/1992 | Alt |
| 5,193,539 A | 3/1993 | Schulman et al. |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,876,423 A | 3/1999 | Braun |
| 5,877,472 A | 3/1999 | Campbell et al. |
| 6,027,456 A | 2/2000 | Feler et al. |
| 6,035,237 A | 3/2000 | Schulman et al. |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,164,284 A | 12/2000 | Schulman et al. |
| 6,172,556 B1 | 1/2001 | Prentice |
| 6,178,353 B1 | 1/2001 | Griffith et al. |
| 6,185,452 B1 | 2/2001 | Schulman et al. |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,249,703 B1 | 6/2001 | Stanton et al. |
| 6,265,789 B1 | 7/2001 | Honda et al. |
| 6,306,100 B1 | 10/2001 | Prass |
| 6,313,779 B1 | 11/2001 | Leung et al. |
| 6,315,721 B2 | 11/2001 | Schulman et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,466,817 B1 | 10/2002 | Kaula et al. |
| 6,505,075 B1 | 1/2003 | Weiner |
| 6,516,227 B1 | 2/2003 | Meadows et al. |
| 6,521,350 B2 | 2/2003 | Fey et al. |
| 6,564,807 B1 | 5/2003 | Schulman et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,652,449 B1 | 11/2003 | Gross et al. |
| 6,662,051 B1 | 12/2003 | Eraker et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mama et al. |
| 6,864,755 B2 | 3/2005 | Moore |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mama et al. |
| 6,986,453 B2 | 1/2006 | Jiang et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,032 B2 | 5/2007 | Schmeling et al. |
| 7,231,254 B2 | 6/2007 | Dilorez |
| 7,234,853 B2 | 6/2007 | Givoletti |
| 7,245,972 B2 | 7/2007 | Davis |
| 7,286,880 B2 | 10/2007 | Olson et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,331,499 B2 | 2/2008 | Jiang et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,496,404 B2 | 2/2009 | Meadows et al. |
| 7,513,257 B2 | 4/2009 | Schulman et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,636,602 B2 | 12/2009 | Baru Fassio et al. |
| 7,640,059 B2 | 12/2009 | Forsberg et al. |
| 7,643,880 B2 | 1/2010 | Tanagho et al. |
| 7,706,889 B2 | 4/2010 | Gerber et al. |
| 7,720,547 B2 | 5/2010 | Denker et al. |

(56) References Cited

U.S. PATENT DOCUMENTS

| | | |
|---|---|---|
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Passover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Hailer et al. |
| 8,180,451 B2 | 5/2012 | Hickman et al. |
| 8,180,452 B2 | 5/2012 | Shaquer |
| 8,180,461 B2 | 5/2012 | Mama et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,612,002 B2 | 12/2013 | Faltys et al. |
| 8,620,436 B2 | 12/2013 | Parramon et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 2002/0116042 A1 | 8/2002 | Boling |
| 2003/0028072 A1 | 2/2003 | Fischell et al. |
| 2003/0078633 A1 | 4/2003 | Firlik et al. |
| 2004/0106963 A1 | 6/2004 | Tsukamoto et al. |
| 2005/0104577 A1 | 5/2005 | Matei et al. |
| 2005/0267546 A1* | 12/2005 | Parramon ............... A61N 1/025 607/48 |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0206166 A1 | 9/2006 | Weiner |
| 2007/0073357 A1 | 3/2007 | Rooney et al. |
| 2007/0265675 A1 | 11/2007 | Lund et al. |
| 2007/0293914 A1 | 12/2007 | Woods et al. |
| 2008/0132961 A1 | 6/2008 | Jaax et al. |
| 2008/0172109 A1 | 7/2008 | Rahman et al. |
| 2008/0183236 A1 | 7/2008 | Gerber |
| 2008/0278974 A1 | 11/2008 | Wu |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0259273 A1 | 10/2009 | Figueiredo et al. |
| 2010/0076254 A1 | 3/2010 | Jimenez et al. |
| 2010/0076534 A1 | 3/2010 | Mock |
| 2011/0152959 A1 | 6/2011 | Sherwood et al. |
| 2011/0270269 A1 | 11/2011 | Swoyer et al. |
| 2011/0276103 A1 | 11/2011 | Maile et al. |
| 2011/0278948 A1 | 11/2011 | Forsell |
| 2011/0282416 A1 | 11/2011 | Hamann et al. |
| 2011/0301667 A1 | 12/2011 | Olson et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0119698 A1 | 5/2012 | Karalis et al. |
| 2012/0130448 A1 | 5/2012 | Woods et al. |
| 2012/0259381 A1 | 10/2012 | Smith et al. |
| 2012/0262108 A1 | 10/2012 | Olson et al. |
| 2012/0274270 A1 | 11/2012 | Dinsmoor et al. |
| 2012/0276854 A1 | 11/2012 | Joshi et al. |
| 2012/0276856 A1 | 11/2012 | Joshi et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0023958 A1 | 1/2013 | Fell |
| 2013/0096651 A1 | 4/2013 | Ozawa |
| 2013/0148768 A1 | 6/2013 | Kim |
| 2013/0150925 A1 | 6/2013 | Vamos et al. |
| 2013/0197608 A1 | 8/2013 | Eiger |
| 2013/0207863 A1 | 8/2013 | Joshi |
| 2013/0211479 A1 | 8/2013 | Olson et al. |
| 2013/0303942 A1 | 11/2013 | Damaser et al. |
| 2013/0310894 A1 | 11/2013 | Trier |
| 2013/0331909 A1 | 12/2013 | Gerber |
| 2014/0222112 A1 | 8/2014 | Fell |
| 2014/0237806 A1 | 8/2014 | Smith et al. |

(56) References Cited

U.S. PATENT DOCUMENTS

| | | |
|---|---|---|
| 2014/0277268 A1 | 9/2014 | Lee |
| 2014/0277270 A1 | 9/2014 | Parramon et al. |
| 2015/0123608 A1 | 5/2015 | Dearden et al. |
| 2015/0214604 A1 | 7/2015 | Zhao et al. |

FOREIGN PATENT DOCUMENTS

| | | |
|---|---|---|
| DE | 102010006837 A1 | 8/2011 |
| EP | 1680182 | 7/2006 |
| EP | 1904153 | 4/2008 |
| EP | 2243509 | 10/2010 |
| JP | 2003-047179 A | 2/2003 |
| JP | 2016512147 | 4/2016 |
| WO | 2000-056677 A1 | 3/2000 |
| WO | 2000-066221 A1 | 11/2000 |
| WO | 2002/003408 A2 | 1/2002 |
| WO | 2002-009808 A1 | 2/2002 |
| WO | 2004-103465 A1 | 12/2004 |
| WO | 2008/021524 | 2/2008 |
| WO | 2009-051539 A1 | 4/2009 |
| WO | 2009-091267 A2 | 7/2009 |
| WO | 2010-042056 A1 | 4/2010 |
| WO | 2010-042057 A1 | 4/2010 |
| WO | 2011/059565 | 5/2011 |
| WO | 2013/141884 | 9/2013 |
| WO | 2014/146016 A2 | 9/2014 |
| WO | 2014/146016 A3 | 1/2015 |

OTHER PUBLICATIONS

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEE, UK, Jan. 1, 1994 (Jan. 1, 1994), pp. 148-152.

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Gundason, G., "A low-power ASK demodulator for Inductively coupled implantable electronics", Solid-State Circuits Conference, 2000, Esscric ''00, Proceedings of the 26rd European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataw ay, NJ, USA, vol. 40, No. 3, Mar. 1, 2005, (Mar. 1, 2005), pp. 763-771.

Sivaprakasam , "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3 ISSN: 0018-9200, Mar. 1, 2005, pp. 763-771.

Tanagho, E., et al., Bladder Pacemaker: Scientific Basis and Clinical Future, Urology, Dec. 1982, vol. 20, No. 6, pp. 614-619.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circutis and Systems, 2006, APCCAS 2006, IEEE Asia Pacific Conference on IEEE, Piscataway, NJ, USA, Dec. 1, 2006 (Dec. 1, 2006), pp. 696-699.

\* cited by examiner

CURRENT SENSING MULTIPLE OUTPUT CURRENT STIMULATORS

CROSS REFERENCE TO RELATED APPLICATION DATA

This application is a continuation of U.S. application Ser. No. 15/263,046 filed Sep. 12, 2016, entitled "CURRENT SENSING MULTIPLE OUTPUT CURRENT STIMULATORS,' which is a divisional of U.S. application Ser. No. 14/217,321 filed Mar. 17, 2014, entitled "CURRENT SENSING MULTIPLE OUTPUT CURRENT STIMULATORS;" and issued as U.S. Pat. No. 9,446,241 on Sep. 20, 2016, which claims the benefit of U.S. Provisional Application No. 61/788,871 filed Mar. 15, 2013; the entirety of each which is hereby incorporated by reference herein.

FIELD OF THE INVENTION

The present invention relates to a current mirror circuit capable of a broad range of uses requiring controlled delivery of electrical current and finding particular utility in functional electrical stimulation (FES) applications.

BACKGROUND OF THE INVENTION

Typically in FES applications, current stimulators are used for providing programmable current pulses directed through an electrode to stimulate targeted neuromuscular tissue. The amplitude and duration of the current pulses delivered through the electrode are usually programmed through a digital to analog converter (DAC). The current output from the DAC is normally amplified to the desired output current amplitude at the current stimulator. The current amplification is typically accomplished using a current mirror circuit and in particular for MOSFET devices, the current gain is achieved by controlling the device semiconductor die width (W) to length (L) ratio (W/L) of the input side and output side transistors of a current mirror. For example, in the prior art current mirror circuit of FIG. 1, the W/L ratios of the input side transistor M1 and the output side transistor M2 determine the overall current gain.

Errors regarding the amplitudes of the current delivered arise mainly due to the finite output impedance of the stimulator and any mismatch errors between the input side transistor M1 and the output side transistor M2. One technique to compensate for the effects of the output impedance of the stimulator is to configure the circuit of FIG. 1 to include transistors MC1 and MC2 in a cascode arrangement in order to increase the output impedance of the stimulator. Typically, to compensate for the mismatch in the input side and output side transistors, the W's and/or L's of the transistors are usually increased. The negative effect however of increasing the device W and L is a marked slow down of the response time of stimulator between turn on to turn off and vice versa by virtue of increased transistor capacitances. This slow down is particularly realized when the stimulator current is programmed for low current amplitudes.

In advanced applications it is contemplated that stimulator output current is to be individually and independently programmed through a plurality of electrodes rather than through just a single electrode. For a candidate circuit as is shown in FIG. 2A, it is contemplated that the cascode transistor may be split into a number of cascode transistors, that is transistors MC(2) to MC(n), supplying output current to respective "loads" and that the overall output current equals the input DAC current times a current gain K. The number of outputs OUT(2) to OUT(n) delivering output current is controllable by switching the gates of the individual cascode transistors to voltage source VBP for turning on a particular transistor and to VS for turning off the particular transistor. In such cases it is likely that individual output currents as well as the overall sum of individual output currents, will vary as a function of different electrode/tissue impedances and the voltages at each of the outputs.

As shown in FIG. 2B, one technique to reduce these variations is to use differential amplifiers or operational amplifiers (op amps) in an attempt to regulate stimulator operation. In such case, one input to the op amp 20 designated as A is the common interconnection of the drains of the cascode transistors MC(2) to MC(n) while another input to the op amp 20 designated as B is a predetermined reference voltage. In operation, the regulated design of FIG. 2B strives to maintain the voltage at input A equal to the voltage at input B for a constant current ID2 flowing through transistor M2 independent of the number of outputs being turned on or off. However this approach could be compromised due to the different loading capacitances and loads coupled to op amp 20 when a different number of electrodes are programmed for current/stimulation delivery. Additionally, long turn on and turn off times are expected especially when relatively small currents are programmed and a large number of electrodes are activated. The situation is compounded especially when using high voltage transistors for the cascode transistors to accommodate high voltages at the outputs. The high voltage transistors usually have high threshold voltages and it normally requires a long time to charge up to the threshold voltage before the transistors turn on. In some instances, what is needed may be a circuit design to improve the output current accuracy for multiple electrode applications without the requirements of continual calibration and a design with less transistor die area. In establishing a current gain K, it may be desirable in at least some instances to avoid dependence on transistor die size to establish the gain and on a more reliable parameter such as resistors.

Furthermore, a design may be helpful in some instances to ensure fast turn on time under different output current levels including small output current delivery conditions especially with a multiplicity of programmable stimulating electrodes that are capable of outputting large current levels. However, in many stimulator designs, the turn on times for delivering small output current levels are usually very long. This is mainly due to the fact that only small currents are available to flow through the transistors for small output current levels to charge the parasitic capacitances of the transistors, especially the gate-to-source capacitances. The turn on times are even longer, especially for high voltage stimulators that can be programmed to have large current outputs. For these high voltage stimulators, very large high voltage transistors are required for the required large output current levels due to the relatively low gain of these transistors. Also, due to the relatively high threshold voltages associated with these high voltage transistors, it will take longer time to have the small current outputs charging up the gate-to-source voltages to higher than the threshold voltages in order to turn on these high voltage transistors.

SUMMARY OF THE INVENTION

One non-limiting embodiment of the present invention includes pairs of transistors, preferably MOSFET transistors, each pair being connected in a current mirror configuration and coupled to a supply transistor in a cascode arrangement. Each pair of transistors has an input side transistor and an output side transistor, the output side transistor of each pair being electrically coupled to a respective and corresponding tissue stimulating electrode. The output side transistors therefore implement a circuit for providing multiple current stimulator capability. The present invention also includes an operational or differential amplifier having one input coupled to a reference voltage and another input coupled to the output side transistors and an output which drives the supply transistor. In steady state, the operational amplifier maintains the voltage at the output side transistor equal to the reference voltage.

In some instances, a current source supplies constant current through a first resistor to establish the reference voltage and a voltage source supplies all the stimulation current through a second resistor to establish the voltage at the output side transistor. A current gain K which represents the factor that multiplies the value of the constant current to provide the total stimulation current is equal to the ratio of the values of the first resistor and the second resistor. In such a manner, the present invention avoids dependency on the MOSFET transistor's width and length values defined in a corresponding semiconductor chip but relies on the more dependable resistor values to achieve the required current gain.

In some instances, advantageously, at circuit turn on, the output of the operational amplifier is very large due to the difference in amplifier input voltages and thus the supply transistor which is driven by the operational amplifier provides large initial currents to discharge the capacitances associated with the output side transistors which results in a major improvement (reduction) in stimulator turn on time almost independent of the number of stimulator outputs.

One embodiment of the present disclosure relates to a peripherally-implantable neurostimulation system. The peripherally-implantable neurostimulation system can include a pulse generator including a reference current generator that generates a reference current, and a multiple output current stimulator circuit. In some embodiments, the multiple output current stimulator circuit can include a current source that can be, for example, connected to the reference current generator. The multiple output current stimulator circuit can include a first resistor coupled to the current source to provide a reference voltage, and at least one output side transistor having a current output terminal for providing an output current. In some embodiments, the multiple output current stimulator circuit can include a second resistor coupled between a voltage source and the at least one output side transistor to thereby provide a common sensing voltage, and a differential amplifier. In some embodiments, the differential amplifier can include a first input coupled to the reference voltage, a second input coupled to the common sensing voltage, and an output arranged to drive the at least one output side transistor as a function of the difference between the reference voltage and the common sensing voltage.

In some embodiments, the peripherally-implantable neurostimulation system can include a lead connected to the pulse generator. This lead can include a plurality of conductive electrodes and plurality of non-conductive regions. In some embodiments of the peripherally-implantable neurostimulation system, the pulse generator can include a plurality of electrical pulse programs that can, for example, affect the frequency and strength of electrical pulses generated by the pulse generator.

In some embodiments, the peripherally-implantable neurostimulation system can include a controller that can communicate with the pulse generator to create one of the plurality of electrical pulse programs and/or a controller that can communicate with the pulse generator to select one of the plurality of electrical pulse programs. In some embodiments, the peripherally-implantable neurostimulation system can include a first switch located between the output of the differential amplifier and the output side transistor. This first switch can be closed according to one of the plurality of electrical pulse programs.

One embodiment of the present disclosure relates to a peripherally-implantable neurostimulation system. The system includes a pulse generator that can generate one or several electrical pulses. The pulse generator can include a current generator that can generate a reference current, and a stimulator that includes a stimulator circuit. In some embodiments, the stimulator circuit amplifies the reference current according to a ratio of resistances of a first resistor and a second resistor. The system can include one or more leads connected to the pulse generator. In some embodiments, the one or more leads can include one or more electrodes and the one or more leads can conduct the one or several electrical pulses from the pulse generator to the one or more electrodes.

In some embodiments of the peripherally-implantable neurostimulation system the stimulator circuit can include a differential amplifier having a first input and a second input. In some embodiments, the first resistor can be coupled to the first input and the second resistor can be coupled to the second input.

In some embodiments the peripherally-implantable neurostimulation system includes a plurality of outputs in electrical connection with the second resistor, and in some embodiments of the system, a stimulator output current flowing through the second resistor is equal to the sum of the current flowing through the outputs. In some embodiments of the peripherally-implantable neurostimulation system, one or both of the first resistor and the second resistor can be a plurality of resistors. In some embodiments of the peripherally-implantable neurostimulation system the plurality of resistors of the first resistor can be arranged in series, and/or in some embodiments, the plurality of resistors of the second resistor can be arranged in parallel.

One embodiment of the present disclosure relates to a peripherally-implantable neurostimulation system. The system includes a pulse generator that can generate one or several electrical pulses. The pulse generator can include a current generator that can generate a reference current, and a stimulator including a stimulator circuit. In some embodiments, the stimulator circuit can include a supply transistor having an output connected to one or several gates of one or several output transistors. The system can include one or more leads connected to the pulse generator, which one or more leads can include one or more electrodes. In some embodiments, the one or more leads can conduct the one or several electrical pulses from the pulse generator to the one or more electrodes.

In some embodiments of the peripherally-implantable neurostimulation system, the drain of the supply transistor can be connected to one or several gates of one or several output transistors. In some embodiments, the peripherally-implantable neurostimulation system can include a differential amplifier. In some embodiments, the output of the differential amplifier can be arranged to drive the supply transistor.

One embodiment of the present disclosure relates to a method of treating neuropathic pain. The method can include implanting a pulse generator in a peripheral portion of a body, which pulse generator can generate one or several electrical pulses. In some embodiments, the pulse generator can include a stimulator circuit that can amplify the reference current according to a ratio of resistances of a first resistor and a second resistor. In some embodiments, the method can include implanting a lead within the peripheral portion of the body, which lead can include one or more electrodes, positioning the one or more electrodes of the lead proximate to a peripheral nerve, and connecting the lead to the pulse generator.

In some embodiments, the method of treating neuropathic pain can further include generating an electrical pulse with the pulse generator; and conducting the electrical pulse to the peripheral nerve with the lead.

One embodiment of the present disclosure relates to a method of treating neuropathic pain. The method can include implanting a pulse generator in a peripheral portion of a body, which pulse generator can generate one or several electrical pulses. In some embodiments, the pulse generator can include a stimulator circuit that can include a supply transistor having an output connected to one or several gates of one or several output transistors. In some embodiments, the method can include implanting a lead within the peripheral portion of the body, which lead can include one or more electrodes, positioning the one or more electrodes of the lead proximate to a peripheral nerve, and connecting the lead to the pulse generator.

In some embodiments, the method of treating neuropathic pain can include generating an electrical pulse with the pulse generator, and conducting the electrical pulse to the peripheral nerve with the lead.

One embodiment of the present disclosure relates to a peripherally-implantable neurostimulation system. The system includes a pulse generator that can generate one or several electrical pulses. The pulse generator can include a current generator that can generate a reference current, and a stimulator that can include a stimulator circuit. In some embodiments, the stimulator circuit has a turn on time of less than 5 us for an output current of less than 50 mA. In some embodiments, the system can include one or more leads connected to the pulse generator. In some embodiments, the one or more leads can include one or more electrodes, which one or more leads can conduct the one or several electrical pulses from the pulse generator to the one or more electrodes.

In some embodiments of the peripherally-implantable neurostimulation system, the turn on time is less than 2 us for an output current between 200 uA and 25 mA. In some embodiments of the peripherally-implantable neurostimulation system, the turn on time is between 0.5 and 2 us for an output current between 200 uA and 25 mA. In some embodiments of the peripherally-implantable neurostimulation system, the pulse generator can generate at least one electrical pulse having a pulse width of 50 us.

One embodiment of the present disclosure relates to a neurostimulation system. The neurostimulation system includes an implantable pulse generator. In some embodiments, the implantable pulse generator includes a first resistance, a reference signal generator that can generate a reference signal, the reference signal being at least one of a reference voltage extending across, or a reference current flowing through the first resistance, and a second resistance. In some embodiments, the neurostimulation system can include a plurality of electrode outputs, and a multi-output stimulator that can amplify the reference signal to a total output signal. In some embodiments, the total output signal can be at least one of a total output voltage or a total output current extending across or flowing through the second resistance. In some embodiments, the multi-output stimulator can distribute the total output signal to at least some of the plurality of electrode outputs. In some embodiments, a gain value of the amplification by the multi-output stimulator is based on the first resistance and the second resistance. In some embodiments, the neurostimulation system can include one or more leads that include a plurality of electrodes that can be coupled to the plurality of electrode outputs.

In some embodiments of the neurostimulation system, the gain value of the amplification by the multi-output stimulator is equal to the first resistance divided by the second resistance. In some embodiments of the neurostimulation system, the first resistance can include a plurality of resistors in series, and in some embodiments, the second resistance can include a plurality of resistors in parallel. In some embodiments of the neurostimulation system, the implantable pulse generator is sized for implantation in a peripheral portion of a human body, and in some embodiments, the peripheral portion of the human body can be one of an arm, a leg, a hand, and a foot.

DETAILED DESCRIPTION OF THE INVENTION

Figure 3:
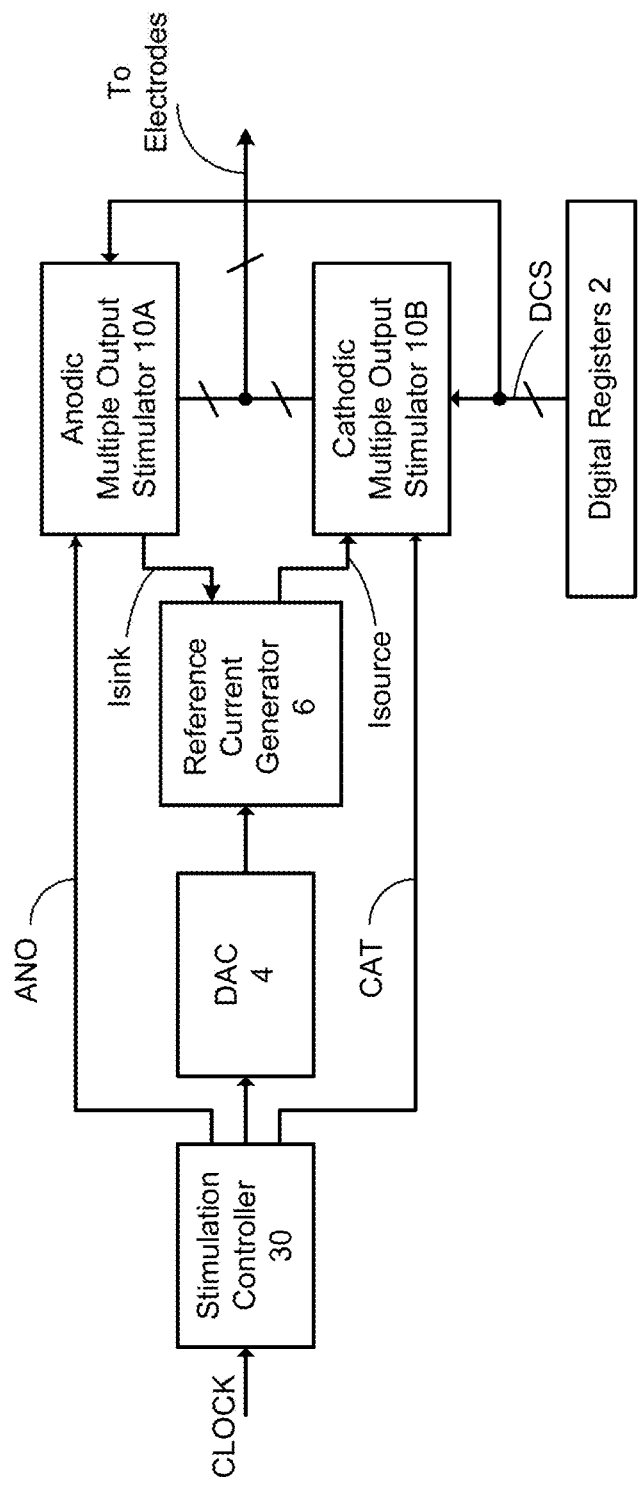
FIG. 3 is an overall block diagram of the multiple output current stimulator system of the present invention.

Referring now to FIG. 3, there is shown an overall block diagram of one example of a multiple output current stimulator system, and specifically, one embodiment of a pulse generator. The system includes both an anodic multiple output stimulator block 10A and a cathodic multiple output stimulator block 10B. The system provides for selecting either an anodic or cathodic stimulator based upon tissue stimulation requirements determined by a clinician. The outputs of the anodic and cathodic stimulators are selected by setting the corresponding "bits" in digital registers 2. Digital registers 2 generate digital control signals DCS, which control the selection of the anodic and cathodic stimulators. Although FIG. 3 discloses two stimulators 10A and 10B, the discussion below with reference to FIGS. 4A and 4B focuses solely on the anodic stimulator 10A. It is to be understood that in some embodiments a complementary circuit for the cathodic stimulator (not shown in FIG. 4A or 4B) functions in accordance with the same principles of operation as does the anodic stimulator and therefore is not included in the following discussion merely for purposes of brevity.

Digital registers 2 also store information regarding stimulation pulse duration, amplitude and profile as well as other operational parameters. Based upon information stored in digital registers 2 and the CLOCK signal, stimulation controller 30 generates the desired stimulation pulse amplitude and triggers digital to analog converter DAC 4 to generate an output. Based upon the DAC 4 output, reference current source generator 6 provides a sink for Isink current (shown as Isink PORT in FIGS. 4A and 4B) for the anodic stimulator and provides a source current Isource for the cathodic stimulator. Stimulation controller 30 generates turn on signal ANO to turn on the anodic stimulator 10A to output anodic current at the selected outputs (OUT(2) to OUT(n) in FIG. 4A and OUT(1) to OUT(n) in FIG. 4B) according to the programmed anodic pulse amplitude, duration and profile. Similarly, stimulation controller 30 also generates turn on signal CAT to turn on cathodic stimulator 10B to output cathodic current at the selected outputs according to the programmed cathodic pulse amplitude, duration and profile.

Figure 4A:
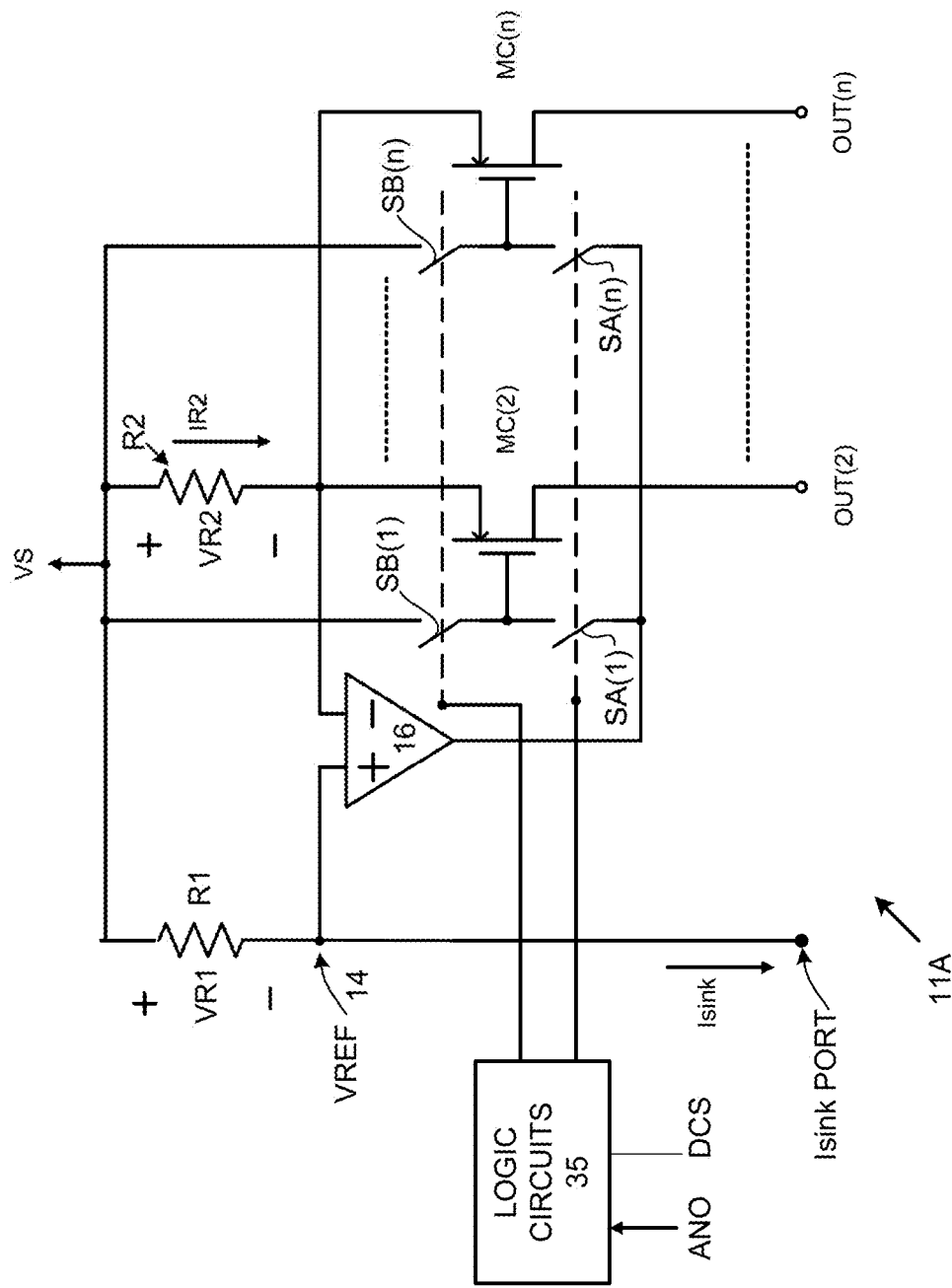
FIG. 4A is a current sensing multiple output stimulator circuit using an op amp and resistor ratios to produce a desired current gain.

With reference to FIG. 4A, a schematic illustration of one non-limiting embodiment of the current sensing multiple output current stimulator circuit 11A is shown. As discussed above, FIG. 4A includes only the anodic multiple output stimulator circuit and it is to be understood that a complementary circuit for cathodic stimulation although not shown in FIG. 4A is to be considered as optionally included in the overall circuit and system. Furthermore, it is to be understood that the invention also contemplates the use of a single multiple output stimulator whether it be for anodic or cathodic stimulation. Upon issuance of signal ANO from stimulation controller 30, current, designated as Isink flows through resistor R1 from voltage source VS and a voltage VR1 is generated across resistor R1 by virtue of the current Isink flowing through R1. Reference voltage VREF 14 is generated as a function of current Isink flowing through resistor R1 and is coupled to the positive input of operational amplifier (op amp) 16. Although the voltage VREF is coupled to the positive input of op amp 16, it is to be understood that reconfiguring the circuit connections to apply VREF to the negative input of op amp 16 is within the contemplation of the invention depending upon complementary circuit designs as may occur when using p channel MOSFET transistors in place of n channel transistors. The current Isink is coupled to reference current generator 6 shown in FIG. 3 via Isink PORT, as shown in FIG. 4A.

Advantageously in some instances, in the embodiment depicted in FIG. 4A, instead of relying on transistor W/L ratios for achieving a desired current gain K, current sensing multiple output current stimulator circuit 11A uses resistors R1 and R2 and opamp 16 to control the gate voltages of the cascode transistors MC(2) to MC(n) for achieving an accurate overall stimulator output current IR2.

Circuit 11A further includes at least one transistor. The source of transistor MC(2) is connected to voltage source VS through resistor R2. The source of transistor MC(2) is also connected to the negative input of op amp 16 and provides a sensing voltage to op amp 16. The drain of transistor MC(2), designated as OUT(2), is coupled to a respective electrode (not shown) for delivery of stimulation current to the tissue in contact with such respective electrode.

As further seen, in FIG. 4A, the op amp 16 is directly connected to the gate terminals of MC(2) to MC(n) through a set of switches SA(1) to SA(n) and SB(1) to SB(n). In some embodiments, these switches can be, for example, "single pole single throw switches." When any of the outputs OUT(2) to OUT(n) are selected to deliver current, the switches SA(1) to SA(n) connected between the op amp 16 output and the corresponding gate terminals of MC(2) to MC(n) are turned on (conducting). In addition, the corresponding switches SB(1) to SB(n) connecting the gate terminals of MC(2) to MC(n) and VS are turned off (not conducting). Switch SA(1) is controlled by logic circuits 35 such that when logic circuits 35 receive signal ANO from controller 30 and digital control signals DCS from digital registers 2, then logic circuits 35 actuate switch SA(1) (causes SA(1) to close) and stimulation current is delivered from output OUT(2) to its respective electrode. When logic circuits 35 de-activate switch SA(1) (causes SA(1) to open), current delivery from output OUT(2) is suspended.

Furthermore, at the same time, to ensure suspension of current delivery from output OUT(2), logic circuits 35 cause switch SB(1) to be activated. Stimulation therapy may be wirelessly controlled by an auxiliary device, such as a remote control or smart phone, to control the timing and duration of the activation of switches SA(1) and SB(1) so as to provide the desired current delivery in accordance with a predetermined therapy protocol. Preferably, logic circuits 35 control the states of switches SA(1) and SB(1) in a complementary fashion such that when switch SA(1) is activated, switch SB(1) is de-activated and vice versa.

Overall switching control can be accomplished by utilizing stimulation controller 30, digital registers 2 and logic circuits 35, either singly or in combination depending upon functional considerations.

In some embodiments, voltage VR1 is generated across resistor R1 when the current Isink flows from voltage source VS through resistor R1. In a like manner, voltage VR2 is generated across R2 when the overall stimulator output current IR2 flows through resistor R2 from voltage source VS. The voltage at the positive input of op amp 16 is the voltage sensed at the sources of transistors MC(1) to MC(n) when the corresponding switches SA(1) to SA(n) are activated and may be considered a common sensing voltage. Uniquely, and due to the feedback loop associated with op amp 16, the voltages at the positive and negative inputs of op amp 16 will be equal in steady state, and therefore, voltage VR2 is forced to be equal to VR1. At steady state, the current IR2 is equal to the sum of the output currents being delivered at all of the outputs OUT(2) to OUT(n). Accordingly, since VR2=IR2·R2 and VR1=Isink·R1, IR2 is equal to Isink·R1/R2 and the required overall current gain K defined as IR2/Isink, is therefore equal to R1/R2. Accordingly, setting the required overall current gain K is a matter of selecting the values of R1 and R2.

In some non-limiting applications, resistors may have better matched characteristics than MOSFETs in an integrated circuit as a function of area. For the same part to part matching accuracy, using resistors as described herein uses less area on an integrated circuit than using MOSFETs. An additional benefit in some instances may arise from the manner in which the resistors R1 and R2 may be constructed. For example, resistor R2 may be made from a number (Np) of parallel resistors and R1 may be made from a number (Ns) of series resistors. Accordingly, for a resistor value R, R1=R·Ns and R2=R/Np and the current gain K=R1/R2=Ns·Np. For the case when Ns=Np=N, the current gain K=$N^2$ and with the total number of resistors equal to 2N (Ns+Np=2N), the total number of resistors as a function of current gain therefore is equal to $2·K^{1/2}$. For a current gain of 100, the number of resistors is 20, whereas a total of 101 individual transistors are required for M1 and M2 (See FIG.

1) since transistors cannot be connected in series for matching transistors connected in parallel. This may be more profound when considering current gains greater than the example K=100 where the saving in die area will be even greater. Still another advantage in some instances relates to the use of the disclosed current gain dependent resistor value technique because no calibration is typically required to achieve the required current gain accuracy and hence providing additional power and die area savings.

Figure 4B:
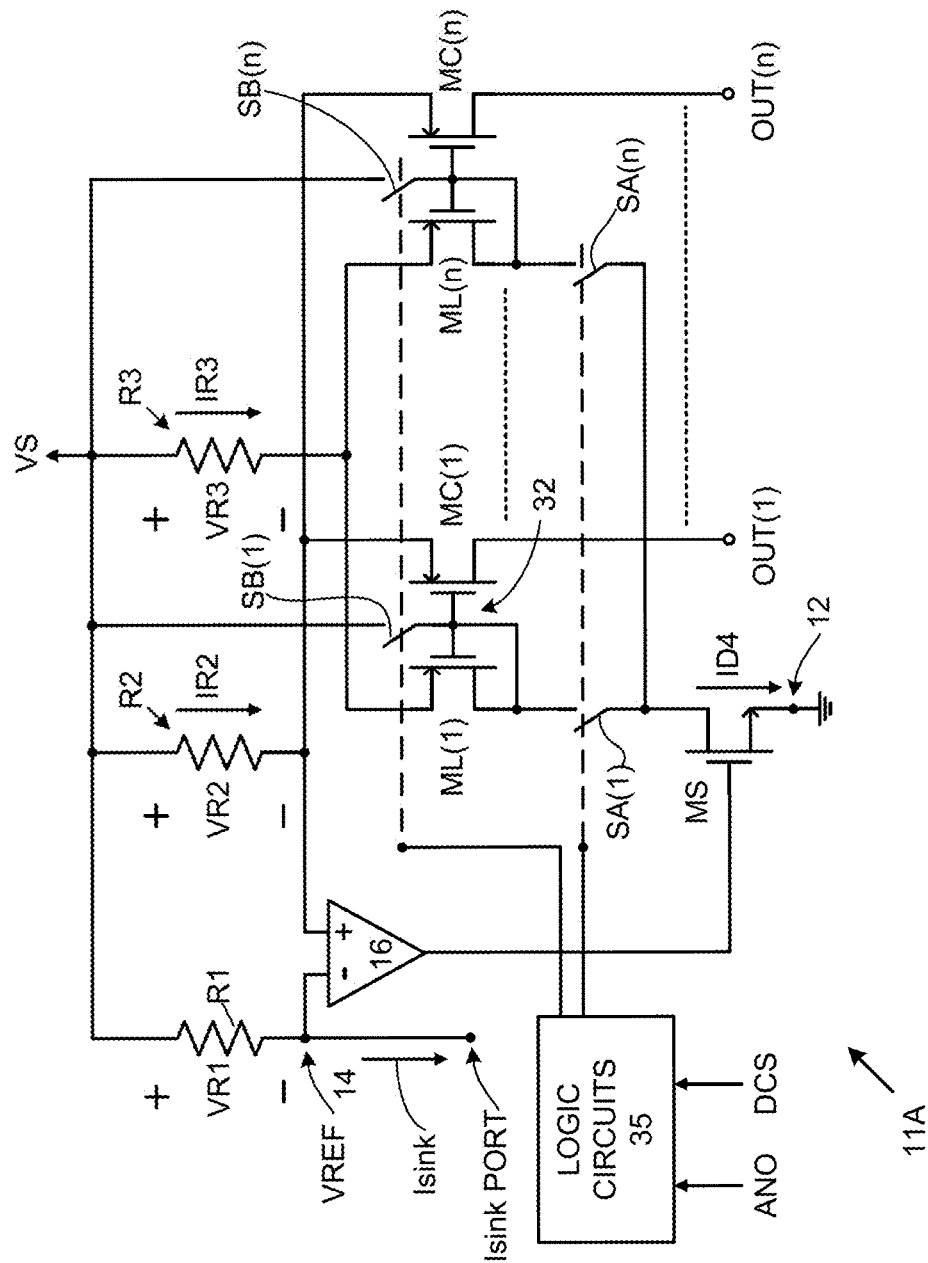
FIG. 4B is a detailed circuit diagram for a current sensing multiple output stimulator circuit of the present invention.

With reference to FIG. 4B, there is shown another embodiment of the current sensing multiple output current stimulator circuit 11B of the present invention. As discussed above, FIG. 4B includes only the anodic multiple output stimulator circuit and it is to be understood that a complementary circuit for cathodic stimulation although not shown in FIG. 4B is to be considered as optionally included in the overall circuit and system. Furthermore, it is to be understood that the invention also contemplates the use of a single multiple output stimulator whether it be for anodic or cathodic stimulation. Upon issuance of signal ANO from stimulation controller 30, current, designated as Isink flows through resistor R1 from voltage source VS and a voltage VR1 is generated across resistor R1 by virtue of the current Isink flowing through R1. Reference voltage VREF 14 is generated as a function of current Isink flowing through resistor R1 and is coupled to the negative input of operational amplifier (op amp) 16. Although the voltage VREF is coupled to the negative input of op amp 16, it is to be understood that reconfiguring the circuit connections to apply VREF to the positive input of op amp 16 is within the contemplation of the invention depending upon complementary circuit designs as may occur when using n channel MOSFET transistors in place of p channel transistors. The current Isink is coupled to reference current generator 6 shown in FIG. 3 via Isink PORT, as shown in FIG. 4B.

Circuit 11B further includes at least one pair of transistors coupled in a current mirror connection arrangement. More specifically, the gate of input side transistor ML(1) is coupled to the gate of output side transistor MC(1) and the commonly connected gate 32 is also connected to the drain of transistor ML(1). The source of transistor MC(1) is connected to voltage source VS through resistor R2 and the source of transistor ML(1) is connected to VS through resistor R3. The source of transistor MC(1) is also connected to the positive input of op amp 16 and provides a sensing voltage to op amp 16. The drain of transistor MC(1), designated as OUT(1), is coupled to a respective electrode (not shown) for delivery of stimulation current to the tissue in contact with such respective electrode.

The current mirror combination of transistors ML(1) and MC(1) is switchably coupled in a cascode arrangement to supply transistor MS through switch SA(1). More specifically, the drain of transistor ML(1) is coupled to one side of a "single pole single throw" switch SA(1) and the drain of transistor MS is coupled to the other side of switch SA(1). The source of transistor MS is coupled to voltage port 12, which for an anodic stimulator is ground and the gate of transistor MS is coupled to the output of op amp 16. For a cathodic stimulator, the voltage port is a voltage source such as VS. Switch SA(1) is controlled by logic circuits 35 such that when logic circuits 35 receive signal ANO from controller 30 and digital control signals DCS from digital registers 2, then logic circuits 35 actuate switch SA(1) (causes SA(1) to close) and stimulation current is delivered from output OUT(1) to its respective electrode. When logic circuits 35 de-activate switch SA(1) (causes SA(1) to open), current delivery from output OUT(1) is suspended.

Furthermore, at the same time, to ensure suspension of current delivery from output OUT(1), logic circuits 35 cause switch SB(1) to be activated. Stimulation therapy may be wirelessly controlled by an auxiliary device, such as a remote control or smart phone, to control the timing and duration of the activation of switches SA(1) and SB(1) so as to provide the desired current delivery in accordance with a predetermined therapy protocol. Preferably, logic circuits 35 control the states of switches SA(1) and SB(1) in a complementary fashion such that when switch SA(1) is activated, switch SB(1) is de-activated and vice versa.

Overall switching control can be accomplished by utilizing stimulation controller 30, digital registers 2 and logic circuits 35, either singly or in combination depending upon functional considerations.

Although the foregoing description relates to a single current mirror combination comprising transistors ML(1) and MC(1), multiple current mirror combinations are contemplated by the present invention. In this regard, FIG. 4B discloses transistor combinations comprising transistors ML(1) to ML(n) and MC(1) to MC(n), where n is the number of the individual current mirror combinations to supply stimulation current to n respective electrodes. As shown in FIG. 4B, each current mirror combination comprising ML(1) and MC(1) to ML(n) and MC(n) is coupled to supply transistor MS through a respective switch SA(1) to SA(n). The commonly connected source of each output side transistor MC(i) provides a common sensing voltage applied to the positive input of op amp 16. The output current delivered from any one output OUT(i) of a respective current mirror combination ML(i) and MC(i) to a respective electrode i, is controlled by digital registers 2 and logic circuits 35 by activating a respective switch SA(i) in accordance with a therapy or stimulation protocol. The protocol may instruct the stimulator to cause any output OUT(i) to provide stimulation current one at a time, or simultaneously in any combination or in any sequence and for any period of time.

As is taught in the prior art for current mirror configurations, input side transistors will exactly mirror the current supplied to it by a current source to the output side transistor only when the transistors are accurately matched (See for example, U.S. Pat. No. 8,575,971). Accordingly, in such cases transistor fabrication requirements place an undue burden on manufacturing and processing techniques resulting in lower device yields and higher device costs. Advantageously, some applications of the present invention obviate the necessity of strict manufacturing processes for establishing transistor width and length dimensions for establishing desired circuit current gain values. As will be discussed below, some embodiments of the present invention rely on selected circuit resistor values to dependably establish required current gain values. More specifically, resistors R1 and R2 in combination with op amp 16 control the gate voltage of supply transistor MS for achieving an accurate overall stimulator output current IR2 flowing through resistor R2. As is to be noted in FIG. 4B, the overall stimulator output current IR2 flowing through resistor R2 is the sum of the currents flowing to outputs OUT(1) through OUT(n) when the corresponding switches SA(1) to SA(n) are activated.

As further shown in FIG. 4B, the common gate connection (shown for example as 32 for ML(1) and MC(1)) of each current mirror coupled pair of transistors ML(i) and MC(i) is connected to voltage source VS through corresponding and respective switch SB(i). The state of the switches SB(1) to SB(n) is determined by logic circuits 35, such that when stimulation current is directed to a specific output OUT(i), the logic circuits 35 cause switch SA(i) to be activated and switch SB(i) to be de-activated, whereby current is delivered to OUT(i) through transistor MC(i). In a similar manner, when stimulation current is to be terminated from a specific output OUT(i), the logic circuits 35 cause switch SA(i) to be de-activated and switch SB(i) to be activated, whereby current delivery from OUT(i) is terminated (suspended).

Voltage VR1 is generated across resistor R1 when the current Isink flows from voltage source VS through resistor R1. In a like manner, voltage VR2 is generated across R2 when the overall stimulator output current IR2 flows through resistor R2 from voltage source VS. The voltage at the positive input of op amp 16 is the voltage sensed at the sources of transistors MC(1) to MC(n) when the corresponding switches SA(1) to SA(n) are activated and may be considered a common sensing voltage. Due to the feedback loop associated with op amp 16, the voltages at the positive and negative inputs of op amp 16 will be equal in steady state, and therefore, voltage VR2 is forced to be equal to VR1. At steady state, the current IR2 is equal to the sum of the output currents being delivered at all of the outputs OUT(1) to OUT(n). Accordingly, since VR2=IR2·R2 and VR1=Isink·R1, IR2 is equal to Isink·R1/R2 and the required overall current gain K defined as IR2/Isink, is therefore equal to R1/R2. Accordingly, setting the required overall current gain K is a matter of selecting the values of R1 and R2.

Figure 1:
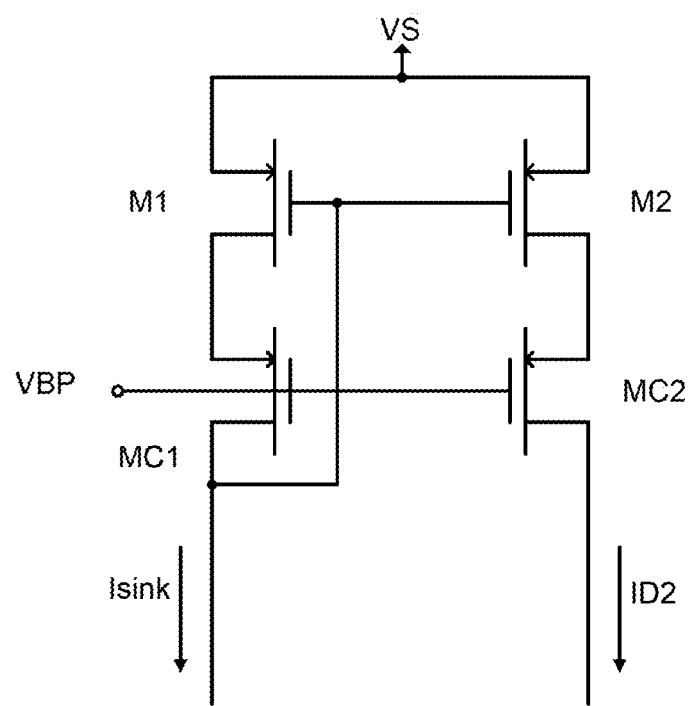
FIG. 1 is a single output stimulator circuit using a cascode current mirror configuration of the prior art.

It is well known that resistors have better matched characteristics than MOSFETs in an integrated circuit for the same area. For the same part to part matching accuracy, using resistors in some applications of the present invention require less area on an integrated circuit than using MOSFETs. An additional benefit arising out of some applications of the present invention, relates to the manner in which the resistors R1 and R2 may be constructed. For example, resistor R2 may be made from a number (Np) of parallel resistors and R1 may be made from a number (Ns) of series resistors. Accordingly, for a resistor value R, R1=R·Ns and R2=R/Np and the current gain K=R1/R2=Ns·Np. For the case when Ns=Np=N, the current gain K=$N^2$ and with the total number of resistors equal to 2N (Ns+Np=2N), the total number of required resistors as a function of current gain therefore is equal to $2·K^{1/2}$. For a required current gain of 100, the number of required resistors is 20, whereas a total of 101 individual transistors are required for M1 and M2 (See FIG. 1) since transistors cannot be connected in series for matching transistors connected in parallel. This may be more profound when considering current gains greater than the example K=100 where the saving in die area will be even greater. Still another advantage of some applications of the present invention relates to the use of the disclosed current gain dependent resistor value technique because no calibration is typically required to achieve the required current gain accuracy and hence providing additional power and die area savings.

In practice, transistors ML(1) and MC(1) are set to have a width (W) to length (L) or W/L ratio of 1:L and the ratio of R3 to R2 is set to L:1. As a result the current IR3 flowing through resistor R3 and hence the current ID4 flowing through transistor MS is approximately equal to the current flowing through resistor R2 (IR2) divided by L or equivalently ID4=Isink·K/L at steady state as the op amp 16 forces VR2 to equal VR1. In this case, the current ID4 is well defined and substantially independent of process and temperature variations.

A further novel advantage of the implementation of op amp 16 in the stimulator circuit 11B in some applications is that during circuit activation, that is, when stimulation controller 30 issues the ANO signal which causes Isink to flow to thereby provide VREF and with IR2 equal to zero amps, the voltage difference between VR1 and VR2 is large such that the output voltage of op amp 16 is very large. It is to be noted however, that logic circuits 35, timed whether it be just prior to or concurrent with the providing of VREF, activate at least one or more preselected switches SA(i) corresponding to the outputs OUT(i) through which current is selected to be delivered. As a consequence, op amp 16 drives supply transistor MS to have a large initial gate to source voltage to thereby produce a large initial drain current ID4. In turn, the gate voltages of the selected transistors MC(i) corresponding to the selected switches SA(i), are drawn down quickly for turning these transistors on quickly. In other words, a large initial current ID4 occurs to discharge the large gate capacitances of selected transistors MC(i) quickly, resulting in a very short stimulator turn on time. The large initial current ID4 is designed to discharge all of the gate capacitances of the selected transistors MC(i).

Figure 2A:
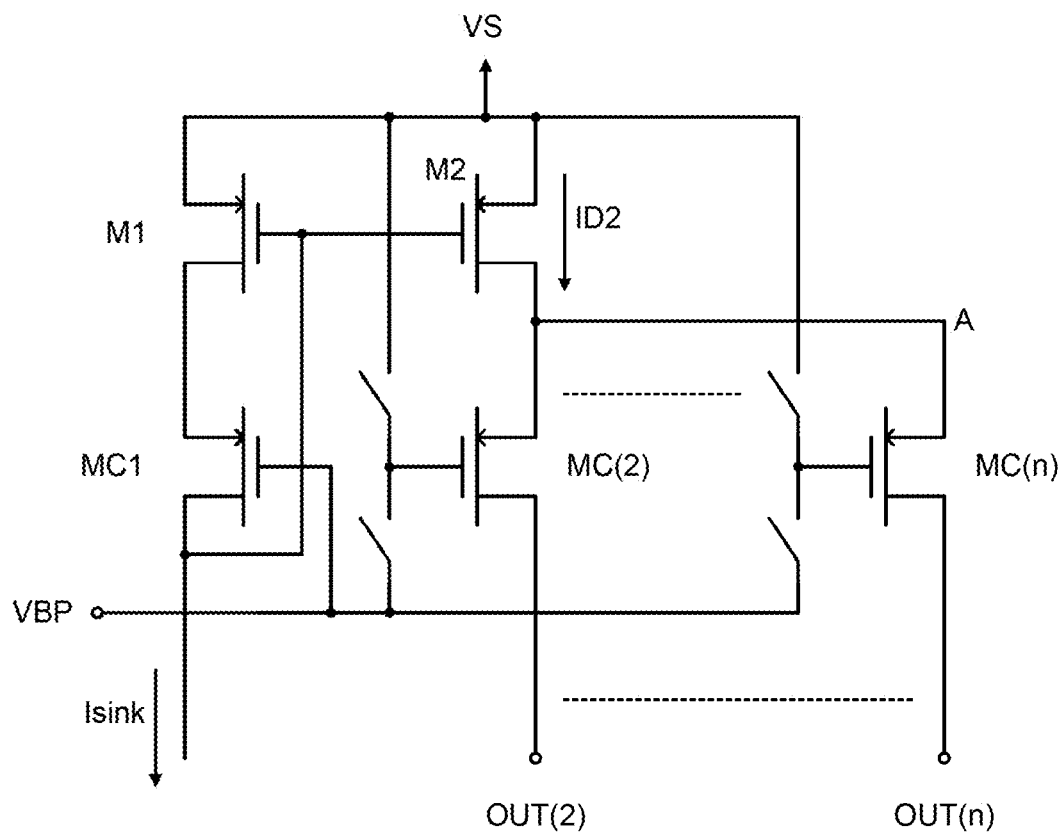
FIG. 2A is a multiple output stimulator circuit using a cascode current mirror.
Figure 2B:
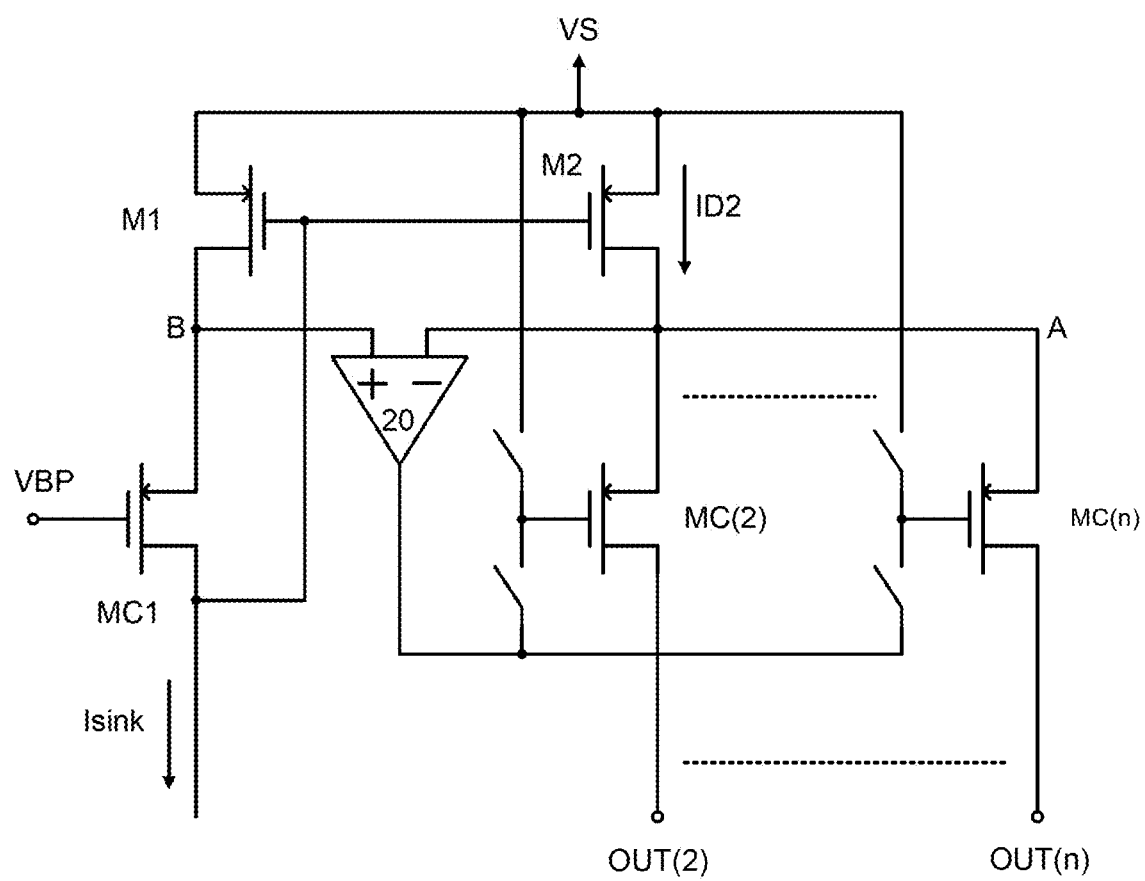
FIG. 2B is a multiple output stimulator circuit using a regulated cascode current mirror.
Figure 5:
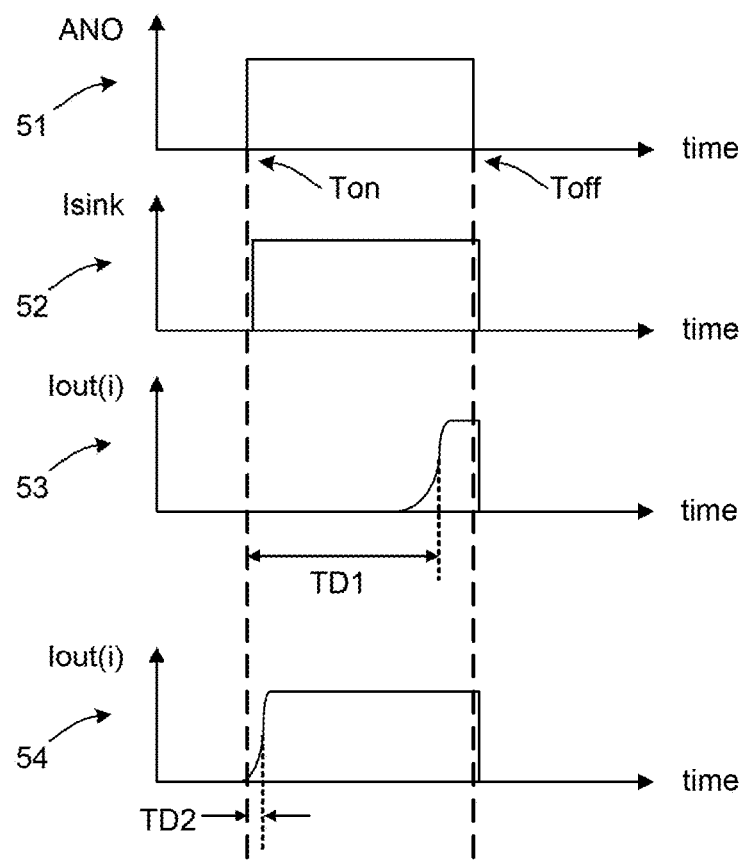
FIG. 5 shows timing diagrams for a multiple output current stimulator with and without the fast turn on time of the present invention.

This novel advantage may be very important in some applications, especially for short output current pulses in some instances. As illustrated in FIG. 5, when the stimulation controller 30 in FIG. 3 generates the signal ANO as shown in waveform 51 with the current Isink output as shown in waveform 52 into reference current generator 6, there will be a significant delay time TD1 as shown in waveform 53 from the rising edge Ton of ANO to one of the stimulator output currents Iout(i) for a stimulator, such as the stimulator of FIG. 2B, that does not have a short turn on time. Nevertheless, as shown in waveform 53, the turn off time for a typical stimulator is almost instantaneous after the falling edge Toff of ANO. As a result, the output current pulse produced by Iout(i) will be significantly shortened from the pulse width defined by the pulse width of ANO as illustrated in waveform 53 of FIG. 5. If the pulse width of ANO is shorter than TD1, Iout(i) will completely disappear. For a typical stimulator design with 8 outputs and a total current output of about 200 uA, TD1 will be over 100 us for a stimulator design based on FIG. 2A that utilizes high voltage transistors for realizing MC(1) to MC(n). In this case, it is assumed that the width-to-length ratio between M(1) and M(2) is 1:100 and the maximum output current of individual outputs (OUT(2) to OUT(n)) is over 25 mA. To support this maximum current at each output, high voltage transistors MC(2) to MC(n) are very large and have very large gate to source capacitances. For typical current stimulators, the shortest pulse is usually longer than 50 us.

Waveform 54 in FIG. 5 shows the benefit of the fast turn on characteristic of one non-limiting application of the present invention in that the time delay TD2 between Ton and the midpoint of the rising edge of current Iout(i) is very short, compared to the much longer time delay TD1 shown in waveform 53 of FIG. 5.

Although it is possible to compensate for the shortening of the current pulses by adjusting the pulse width of ANO to be TD1 longer than the desired pulse width, the delay time TD1 is often dependent on the amplitudes (or levels) of Iout(i) and/or the total output current IR2 into all the stimulation electrodes. Furthermore, there will be variations in TD1 between different stimulators implemented in different ICs due to process variations. Therefore, it is very difficult to correctly compensate for the delay time TD1 by adjusting the pulse width of ANO. In some embodiments, it may be advantageous to have a pulse generator that is capable of short turn on time over a range of output currents. In one embodiment, for example, the pulse generator may have turn on times less than 10 us, 5 us, 2 us, 1 us or any other or intermediate value and/or between, approximately 0.1 and 2 us, 0.1 and 4 us, 0.1 and 10 us, 0.1 and 20 us, 0.2 and 16 us, 0.3 and 12 us, 0.4 and 8 us, 0.5 and 6 us, 0.5 and 4 us, 0.5 and 2 us, 0.5 and 1 us, or any other or intermediate turn on time. In some embodiments, these turn on times can be achieved for output currents of less than 100 mA, 75 mA, 50 mA, 25 mA, or any other or intermediate current, and/or between 50 uA and 100 mA, 100 uA and 75 mA, 150 uA and 50 mA, 200 uA and 25 mA, 500 uA and 10 mA, or any other or intermediate current. In some embodiments, and as used above, approximately can comprise 10 percent of the defined range. FIG. 4B depicts on embodiment of a circuit 11B with a short turn on time. In FIG. 4B, circuit 11B has a turn on time in the range of 0.5-2 us for a total output current IR2 ranging between 200 uA and 25 mA for the number of working outputs being between 1 and 8. Even without any compensation of the pulse width of ANO, this short turn on time is quite tolerable even for the shortest pulse width of 50 us.

For the embodiment shown in FIG. 4B, the op amp frequency response is independent of the overall current IR2 and the number of outputs being turned on since the output of the op amp is only connected to the gate terminal of the supply transistor MS. Furthermore, due to the large initial current ID4 on the supply transistor as mentioned above, MC(1) to MC(n) are drawn down quickly for turning these transistors on quickly without using a high current driving capability op amp. Therefore, the turn on time of the present invention of FIG. 4B will be much shorter than that of the stimulator based on the circuit topology of FIG. 4A.

Circuit 11A, 11B can be used in a variety of stimulation devices. In one embodiment, the above mentioned advantages of circuit 11A, 11B enable use of circuit 11A, 11B in a peripherally-implantable neurostimulation system for treating neuropathic pain or for other uses.

Approximately 8% of the Western (EU and US) population is affected by Neuropathic pain (chronic intractable pain due to nerve damage). In about 5% of people, this pain is severe. There are at least 200,000 patients that have chronic intractable pain involving a nerve. Neuropathic pain can be very difficult to treat with only half of patients achieving partial relief. Thus, determining the best treatment for individual patients remains challenging. Conventional treatments include certain antidepressants, anti-epileptic drugs and opioids. However, side effects from these drugs can be detrimental. In some of these cases, electrical stimulation, including FES, can provide effect treatment of this pain without the drug-related side effects.

A spinal cord stimulator, which is one type of FES device, is a device used to deliver pulsed electrical signals to the spinal cord to control chronic pain. Because electrical stimulation is a purely electrical treatment and does not cause side effects similar to those caused by drugs, an increasing number of physicians and patients favor the use of electrical stimulation over drugs as a treatment for pain. The exact mechanisms of pain relief by spinal cord stimulation (SCS) are unknown. The scientific background of the SCS trials was based initially on the Gate Control Theory of pain that was first described by Melzack and Wall in 1965. The theory posits that pain is transmitted by two kinds of afferent nerve fibers. One is the larger myelinated Aδ fiber, which carries quick, intense-pain messages. The other is the smaller, unmyelinated "C" fiber, which transmits throbbing, chronic pain messages. A third type of nerve fiber, called Aβ, is "non-nociceptive," meaning it does not transmit pain stimuli. The gate control theory asserts that signals transmitted by the Aδ and C pain fibers can be thwarted by the activation/stimulation of the non-nociceptive Aβ fibers and thus inhibit an individual's perception of pain. Thus, neurostimulation provides pain relief by blocking the pain messages before they reach the brain.

At the present time, SCS is used mostly in the treatment of failed back surgery syndrome, a complex regional pain syndrome that has refractory pain due to ischemia. SCS complications have been reported in 30% to 40% of all SCS patients. This increases the overall costs of patient pain management and decreases the efficacy of SCS. Common complications include: infection, hemorrhaging, injury of nerve tissue, placing device into the wrong compartment, hardware malfunction, lead migration, lead breakage, lead disconnection, lead erosion, pain at the implant site, generator overheating, and charger overheating. The occurrence rates of common complications are surprisingly high: 9.5% are accounted for lead extension connection issues, 6% are due to lead breakage, 22.6% of cases are associated with lead migration and 4.5% experienced infection.

Peripheral neuropathy may be either inherited or acquired. Causes of acquired peripheral neuropathy include physical injury (trauma) to a nerve, viruses, tumors, toxins, autoimmune responses, nutritional deficiencies, alcoholism, diabetes, and vascular and metabolic disorders. Acquired peripheral neuropathies are grouped into three broad categories: those caused by systemic disease, those caused by trauma, and those caused by infections or autoimmune disorders affecting nerve tissue. One example of an acquired peripheral neuropathy is trigeminal neuralgia, in which damage to the trigeminal nerve (the large nerve of the head and face) causes episodic attacks of excruciating, lightning-like pain on one side of the face.

A high percentage of patients with peripheral neuropathic pain do not benefit from SCS for various reasons. However, many of these patients can receive acceptable levels of pain relief via direct electrical stimulation to the corresponding peripheral nerves. This therapy is called peripheral nerve stimulation (PNS). There is, however, no FDA approved PNS devices in the US market. Standard spinal cord stimulator (SCS) devices are often used off label by pain physicians to treat this condition. It is estimated that about 15% of SCS devices have been used off-label for PNS.

As current commercially-available SCS systems were designed for stimulating the spinal cord and not for peripheral nerve stimulation, there are more device complications associated with the use of SCS systems for PNS than for SCS. Current SCS devices (generators) are large and bulky. In the event that an SCS is used for PNS, the SCS generator is typically implanted in the abdominal or in the lower back above the buttocks and long leads are tunneled across multiple joints to reach the target peripheral nerves in the arms, legs or face. The excessive tunneling and the crossing of joints leads to increased post-surgical pain and higher device failure rates. Additionally, rigid leads can lead to skin erosion and penetration, with lead failure rates nearing 100% within 3 years of implantation. Most complications result in replacement surgery and even multiple replacement surgeries in some cases.

Figure 6:
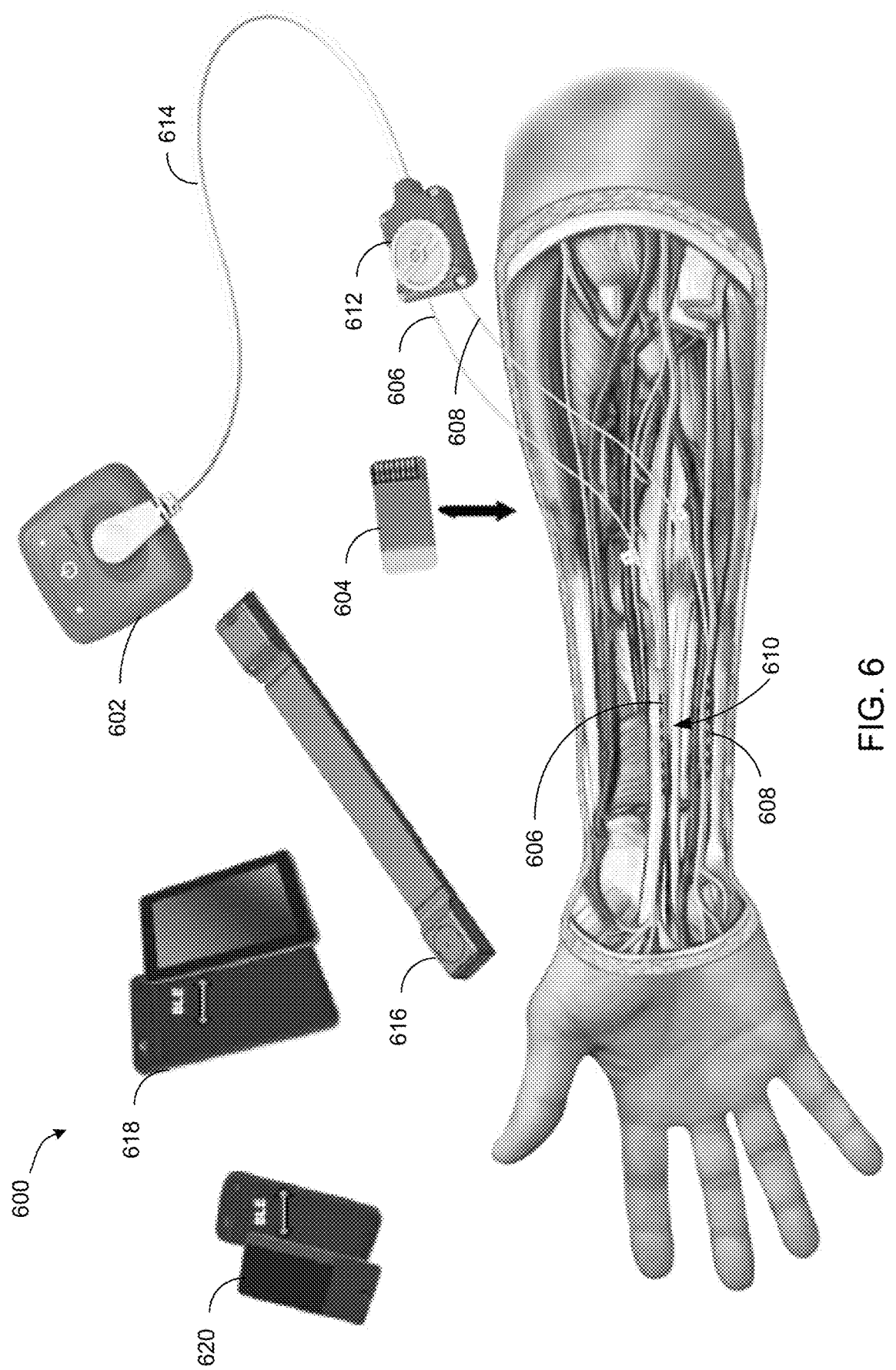
FIG. 6 is a schematic illustration of one embodiment of a peripherally-implantable neurostimulation system.

One embodiment of a peripherally-implantable neurostimulation system 600 is shown in FIG. 6. In some embodiments, the peripherally-implantable neurostimulation system 600 can be used in treating patients with, for example, chronic, severe, refractory neuropathic pain originating from peripheral nerves. In some embodiments, the peripherally-implantable neurostimulation system 600 can be used to either stimulate a target peripheral nerve or the posterior epidural space of the spine.

The peripherally-implantable neurostimulation system 600 can include one or several pulse generators. The pulse generators can comprise a variety of shapes and sizes, and can be made from a variety of materials. In some embodiments, the one or several pulse generators can generate electrical pulses that are delivered to the nerve to control pain. In some embodiments, a pulse generator can be an external pulse generator 602 or an implantable pulse generator 604. In some embodiments, an external pulse generator 602 can be used to evaluate the suitability of a patient for treatment with the peripherally-implantable neurostimulation system 600 and/or for implantation of an implantable pulse generator 604.

The implantable pulse generator 604 can be sized and shaped, and made of material so as to allow implantation of the implantable pulse generator 604 inside of a body. In some embodiments, the implantable pulse generator 604 can be sized and shaped so as to allow placement of the implantable pulse generator 604 at any desired location in a body, and in some embodiments, placed proximate to peripheral nerve such that leads (discussed below) are not tunneled across joints and/or such that extension cables are not needed. In some embodiments, the pulse generator, and specifically the implantable pulse generator 604 and/or the external pulse generator 602 can incorporate one of the circuits 11A, 11B, as shown in either or both of the embodiments of FIGS. 4A and 4B.

In some embodiments, the electrical pulses generated by the pulse generator can be delivered to one or several nerves 610 and/or to tissue proximate to one or several nerves 610 via one or several leads. The leads can include conductive portions, referred to as electrodes, and non-conductive portions. The leads can have a variety of shapes, be a variety of sizes, and be made from a variety of materials, which size, shape, and materials can be dictated by the application or other factors.

In some embodiments, the leads can include an anodic lead 606 and/or a cathodic lead 608. In some embodiments, the anodic lead 606 and the cathodic lead 608 can be identical leads, but can receive pulses of different polarity from the pulse generator.

In some embodiments, the leads can connect directly to the pulse generator, and in some embodiments, the leads can be connected to the pulse generator via a connector 612 and a connector cable 614. The connector 612 can comprise any device that is able to electrically connect the leads to the connector cable 614. Likewise, the connector cable can be any device capable of transmitting distinct electrical pulses to the anodic lead 606 and the cathodic lead 608.

In some embodiments, the peripherally-implantable neurostimulation system 600 can include a charger 616 that can be configured to recharge the implantable pulse generator 604 when the implantable pulse generator 604 is implanted within a body. The charger 616 can comprise a variety of shapes, sizes, and features, and can be made from a variety of materials. In some embodiments, the charger 616 can recharge the implantable pulse generator 604 via an inductive coupling.

In some embodiments, details of the electrical pulses can be controlled via a controller. In some embodiments, these details can include, for example, the frequency, strength, pattern, duration, or other aspects of the timing and magnitude of the electrical pulses. This control of the electrical pulses can include the creation of one or several electrical pulse programs, plans, or patterns, and in some embodiments, this can include the selection of one or several pre-existing electrical pulse programs, plans, or patterns. In the embodiment depicted in FIG. 6, the peripherally-implantable neurostimulation system 600 includes a controller that is a clinician programmer 618. The clinician programmer 618 can be used to create one or several pulse programs, plans, or patterns and/or to select one or several of the created pulse programs, plans, or patterns. In some embodiments, the clinician programmer 618 can be used to program the operation of the pulse generators including, for example, one or both of the external pulse generator 602 and the implantable pulse generator 604. The clinician programmer 618 can comprise a computing device that can wiredly and/or wirelessly communicate with the pulse generators. In some embodiments, the clinician programmer 618 can be further configured to receive information from the pulse generators indicative of the operation and/or effectiveness of the pulse generators and the leads.

In some embodiments, the controller of the peripherally-implantable neurostimulation system 600 can include a patient remote 620. The patient remote 620 can comprise a computing device that can communicate with the pulse generators via a wired or wireless connection. The patient remote 620 can be used to program the pulse generator, and in some embodiments, the patient remote 620 can include one or several pulse generation programs, plans, or patterns created by the clinician programmer 618. In some embodiments, the patient remote 620 can be used to select one or several of the pre-existing pulse generation programs, plans, or patterns and to select, for example, the duration of the selected one of the one or several pulse generation programs, plans, or patterns.

Advantageously, the above outlined components of the peripherally-implantable neurostimulation system 600 can be used to control and provide the generation of electrical pulses to mitigate patient pain.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A method of providing stimulation comprising:
    implanting a pulse generator configured to generate one or several electrical pulses in a portion of a body, the pulse generator comprising a stimulator circuit, wherein the stimulator circuit comprises a supply transistor having a gate connected to a differential amplifier and an output connected to a gate of each of a plurality of output transistors;
    implanting a lead within the portion of the body, wherein the lead comprises one or more electrodes;
    positioning the one or more electrodes of the lead proximate to a nerve; and
    connecting the lead to the pulse generator.

2. The method of providing stimulation of claim 1, further comprising generating an electrical pulse with the pulse generator; and conducting the electrical pulse to the nerve with the lead.

3. The method of providing stimulation of claim 1, wherein the stimulator circuit further comprises a current source.

4. The method of providing stimulation of claim 3, wherein the pulse generator further comprises a switching control circuit.

5. The method of providing stimulation of claim 4, wherein the switching control circuit is configured to control a plurality of switches, each of the plurality of switches configured to selectively couple the output of the supply transistor to at least one of the one or several gates of the one or several output transistors.

6. The method of providing stimulation of claim 5, wherein the pulse generator comprises a stimulation controller.

7. The method of providing stimulation of claim 6, further comprising generating a turn on signal with the stimulation controller.

8. The method of providing stimulation of claim 7, wherein an electrical pulse of the one or several electrical pulses is generated in response to receipt of the turn on signal.

9. The method of providing stimulation of claim 8, wherein generating the one or several electrical pulses comprises: driving the supply transistor to produce a turn on time of the stimulator circuit of less than 5 µs for the electrical pulse having a current of less than 50 mA.

10. The method of providing stimulation of claim 8, wherein generating the one or several electrical pulses comprises: driving the supply transistor to produce a turn on time of the stimulator circuit of less than 2 µs for the electrical pulse having a current between 200 µA and 25 mA.

11. The method of providing stimulation of claim 8, wherein the one of the one or several electrical pulses has a pulse width of 50 µs.

12. The method of providing stimulation of claim 8, wherein the differential amplifier comprises an output arranged to drive the supply transistor as a function of a difference between a reference voltage and a common sensing voltage.

13. The method of providing stimulation of claim 12, wherein the switching control circuit controls the reference voltage such that the reference voltage is provided upon activation of at least one switch of the plurality of switches to thereby discharge capacitances related to an output side transistor corresponding to the at least one activated switch.

14. The method of providing stimulation of claim 13, wherein upon providing the reference voltage, the differential amplifier drives the supply transistor so as to discharge capacitances related to the output side transistor corresponding to the at least one activated switch.

15. A method of providing stimulation comprising:
implanting a pulse generator configured to generate one or several electrical pulses in a portion of a body, the pulse generator comprising a switching control circuit and a stimulator circuit, wherein the stimulator circuit comprises a supply transistor having an output connected to one or several gates of one or several output transistors, wherein the switching control circuit is configured to control a plurality of switches, each of the plurality of switches configured to selectively couple the output of the supply transistor to at least one of the one or several gates of the one or several output transistors;
implanting a lead within the portion of the body, wherein the lead comprises one or more electrodes;
positioning the one or more electrodes of the lead proximate to a nerve;
connecting the lead to the pulse generator;
receiving switch control signals; and
selectively coupling the output of the supply transistor to at least one of the one or several gates of the one or several output transistor according to the switch control signals.

16. A method of providing stimulation comprising:
implanting a pulse generator configured to generate one or several electrical pulses in a portion of a body, the pulse generator comprising at least one input side transistor; at least one output side transistor, a switching control circuit, and a stimulator circuit, wherein the stimulator circuit comprises a supply transistor having an output connected to one or several gates of one or several output transistors, wherein the switching control circuit is configured to control a plurality of switches, each of the plurality of switches configured to selectively couple the output of the supply transistor to at least one of the one or several gates of the one or several output transistors;
implanting a lead within the portion of the body, wherein the lead comprises one or more electrodes;
positioning the one or more electrodes of the lead proximate to a nerve;
connecting the lead to the pulse generator.

17. The method of providing stimulation of claim 16, wherein the output side transistor is current mirror coupled to the at least one input side transistor, and wherein the at least one output side transistor has a current output terminal for providing an output current.

* * * * *